US005824852A

United States Patent [19]
Francis

[11] Patent Number: 5,824,852
[45] Date of Patent: Oct. 20, 1998

[54] INBRED CORN LINE NP 2013

[75] Inventor: Thomas R. Francis, London, Canada

[73] Assignee: Novartis Finance Corporation, New York, N.Y.

[21] Appl. No.: 802,021

[22] Filed: Feb. 18, 1997

[51] Int. Cl.$^6$ ................................ A01H 5/00; A01H 4/00; A01H 1/00; C12N 5/04
[52] U.S. Cl. .................. 800/200; 800/250; 800/DIG. 56; 47/58; 47/DIG. 1; 435/412; 435/424; 435/430; 435/430.1
[58] Field of Search ...................................... 800/200, 205, 800/235, 250, DIG. 56; 435/172.3, 172.1, 412, 424, 430, 430.1; 47/58

Primary Examiner—Gary Benzion
Assistant Examiner—Melissa L. Kimball
Attorney, Agent, or Firm—Thomas Hoxie

[57] ABSTRACT

An inbred corn line, designated NP 2013, is disclosed. The invention relates to the seeds of inbred corn line NP 2013, to the plants of inbred corn line NP 2013 and to methods for producing a corn plant produced by crossing inbred line NP 2013 with itself or with another corn plant. The invention further relates to hybrid corn seeds and plants produced by crossing inbred line NP 2013 with another corn line.

18 Claims, No Drawings

INBRED CORN LINE NP 2013

BACKGROUND OF THE INVENTION

This invention relates to a new and distinctive corn inbred line designated NP 2013 and to hybrids made by using NP 2013 as a parent.

Corn (*Zea mays*) is a valuable and important field crop. Thus, plant breeders are continually developing new and superior corn inbred lines for production of high yielding, agronomically sound hybrids. The goal of the plant breeder is to combine in a single variety or hybrid an improved combination of desirable traits from the parent, inbred germplasm. These traits may include maximization of yield, resistance to disease and insects, tolerance to drought, heat and other environmental stresses. These traits are governed by a complex genetic system that makes selection and breeding of an inbred line challenging.

Corn hybrid development requires the development of homozygous inbred lines, the crossing of these lines, and the subsequent evaluation of those crosses. Pedigree, backcross, and recurrent selection breeding methods are used to develop inbred lines from breeding populations. Breeding programs combine the genetic backgrounds from two or more inbred lines or various other genetic sources into breeding pools from which new inbred lines are developed by self pollination and selection of desired phenotypes. The new inbred lines are crossed with other inbred lines, and hybrids from these crosses are evaluated to determine which have commercial potential.

Once the inbred parents that give a superior hybrid are identified, the hybrid seed can be reproduced indefinitely as long as inbred parent homogeneity is maintained. Corn hybrids may be either single cross hybrids, produced when two inbred lines are crossed to produce the first generation ($F_1$) progeny; double cross hybrids, produced from four inbred lines crossed in pairs (A×B and C×D) and then the two $F_1$ hybrids are crossed again (A×B)×(C×D); or three-way cross hybrids produced from crossing a single cross (A×B) to a third inbred line C. Numerous references are available on the topic of corn breeding and hybrid seed corn production. Those skilled in the art of corn breeding and production are well aware of techniques and methods for the development of inbred corn lines and corn hybrids. However, while many of the techniques and methods are known, breeder care and expertise must be used in the selection of breeding material for resulting yield increase and superior agronomic traits. Reference is made particularly to Corn and Corn Improvement, Third Edition, ed. G. F. Sprague and J. W. Dudley, American Society of Agronomy Monograph No. 18, particularly chapters 8 and 9, the substantive content of which is hereby incorporated by reference.

SUMMARY OF THE INVENTION

According to the invention, there is provided a novel inbred corn line, designated NP 2013. This invention thus relates to the seeds of inbred corn line NP 2013, to the plants of inbred corn line NP 2013 and to methods of producing a corn plant comprising the crossing of inbred corn line NP 2013 with itself or another corn line.

This invention further relates to hybrid corn seed produced by crossing the inbred line NP 2013 with another corn inbred line. More specifically the invention extends to hybrid corn seed produced by planting in pollinating proximity seeds of inbred corn line NP 2013 and a second inbred line having a genotype different from NP 2013; cultivating corn plants resulting from said planting until time of flowering; emasculating the flowers of plants of one of the inbred lines; allowing cross pollination to occur between the inbred lines; and harvesting seeds produced on the plants of the inbred line. The hybrid plants grown from the seed produced as stated above.

DEFINITIONS

In the description and examples that follow a number of terms are used; therefore, to provide a clear and consistent understanding of the specification and claims the following definitions are provided.

RK=Round Kernels: the percentage of kernels that do not pass through a 13/64 slotted screen.

HE=Husk Extension: the length (cm) of the husk past the ear tip at maturity.

NN=Node Number: the number of nodes of the entire plant.

PRM=Predicted Relative Maturity. This trait is based on the harvest moisture of the grain. The relative maturity rating is based on a known set of checks, and is referred to as the Minnesota Relative Rating System.

MST=Harvest Moisture. The moisture is the actual percentage moisture of the grain at harvest.

STK (BR)=The percentage of plants broken below the ear at harvest.

YLD=Yield; bushels per acre. The actual yield of the grain at harvest (bu/a) adjusted to approximately 15.5% moisture.

RT=Number of plants lodged (leaning from vertical but not broken).

Plt. Ht.=Plant Height. The length of the plant to tassel tip (cm).

GRQU=Grain Quality. A rating for the general appearance of the shelled grain as it is harvested based on factors such as the color of the harvested grain, mold on the grain and any cracked grain. The rating is based on a scale of 1 to 9 wherein 1 indicates high grain quality and 9 indicates the lowest.

INTL=Late Season Intactness. The degree to which portion of the plant above the ear remains intact and erect at harvest. The rating is based on a scale of 1 to 9 wherein 1 is most intact.

HU=Heat Units;

$$\frac{\text{Max Temp } (\leq 86^\circ \text{ F.}) + \text{Min Temp } (\geq 50^\circ \text{ F.})}{2} - 50$$

HUS=Heat units from emergence to 50% of plants in silk.

HU to pollen=Heat units from emergence to 50% of plants in pollen.

HU to pollen shed=Heat units from 10% to 90% pollen shed.

Ear Ht.=Ear Height. The measurement from the ground to the top developed ear node attachment measured in cm.

STGR=Stay Green. The measure of plant health near the time of black layer formation (physiological maturity). The rating is based on a scale of 1 to 9 wherein 1 indicates better late-season plant health.

DETAILED DESCRIPTION OF THE INVENTION

Inbred corn line NP 2013 is a yellow dent inbred line with superior characteristics and is best suited as a female in crosses for production of first generation ($F_1$) corn hybrids. NP 2013 is best adapted to the Northeast region of the U.S. NP 2013 can be used to produce hybrids from approximately 75–95 PRM days based on the Minnesota Relative Maturity Rating System for harvest of grain. Inbred line NP 2013 has demonstrated good combining ability with families derived from Iowa Stiff Stalk Synthetic, CM7 and W117.

Inbred corn line NP 2013 was derived from crossing Northrup King line NP 761×L8501. Self -pollination and standard pedigree ear-to-row breeding were practiced within the above population for seven generations in the development of NP 2013. During the development of the line, crosses of segregating families were made to inbred testers to evaluate combining ability. Inbred line NP 2013 can be reproduced by planting seeds of the line, growing the resulting corn plants under self-pollination or sib-pollination conditions with adequate isolation and then harvesting the resulting seed. No variant traits have been observed or are expected in NP 2013. Inbred line NP 2013 can be reproduced using techniques famialr to those skilled in the art of plant breeding and generally can be described as planting seeds of the line, growing the resulting plants under standard conditions of self-pollination or sib-pollination with adequate isolation and harvesting the seeds.

The inbred line has been evaluated at numerous research stations across the U.S. and Canada. Inbred line NP 2013 has shown uniformity and stability for all discernible characteristics as described in the following variety description. The description is based on data collected primarily at London, Ont., Stanton, Minn. and Janesville, Wis., on a maximum of 2 replications in 1994 and 1995. In interpreting the color designations herein, reference is made to the Munsell Glossy Book of Color, a standard color reference to describe all color choices.

TABLE 1

VARIETY DESCRIPTION INFORMATION FOR INBRED LINE NP 2013 and A 619

|  | NP 2013 | A 619 |
|---|---|---|
| Type: | Dent | Dent |
| Region Best Adapted: | Northeastern | Northern and Central |
| A. Maturity: | | |
| HU to 50% Silk (HUS): | 1203 | 1281 |
| HU to 50% pollen shed: | 1166 | 1258 |
| Plant Characteristics: | | |
| Plant height (to tassel tip) (cm): | 168.5 | 191.8 |
| Plant height to top ear node (cm): | 54.2 | 49 |
| Number of tillers: | 0 | 0.3 |
| Number of ears per stalk: | 1.3 | 1.2 |
| Cytoplasm type: | Normal | Normal |
| Anthocyanin of brace roots: | Faint | Faint |
| C. Leaf: | | |
| Color of second leaf above the ear (at anthesis) | Dark-green (3)(5) (5GY 4/8) | Medium-green (3) (5) (5GY 5/8) |
| Leaf angle (from 2nd leaf above ear at anthesis to stalk above leaf) | 43° | 45.8° |
| Number of leaves- above top ear node, (mature plants): | 4.5 | 5.6 |
| Marginal waves: (Scale: 1 = none to 9 = many): | 3.3 | 4.8 |
| Width (widest point of top ear node leaf) (cm): | 7.5 | 8.9 |
| Sheath Pubescence: (Scale 0 = none to 9 = many): | 5.1 | 1.8 |
| Longitudinal creases: | 3.6 | 3.9 |

TABLE 1-continued

VARIETY DESCRIPTION INFORMATION FOR INBRED LINE NP 2013 and A 619

|  | NP 2013 | A 619 |
|---|---|---|
| (Scale: 1 = none to 9 = heavy): | | |
| Length (ear node leaf) (cm): | 61.7 | 68.3 |
| D. Tassel: | | |
| Number of primary lateral branches: | 6.6 | 8.0 |
| Branch angle of secondary primary lateral branch at anthesis: | 40° | 42.8° |
| Anther color: | Tan (2.5Y 7/6) | Yellow (5Y 8/6) |
| Glume color: | Light-green (5GY 6/6) | Medium-green (5GY 5/8) |
| Bar glumes: | present | present |
| Tassel length (from top leaf collar to tassel tip): | 41.0 | 42.3 |
| E. Ear (Husked ear data except wherestated otherwise): | | |
| Length (cm): | 15.4 | 15.0 |
| Weight (gm): | 90.8 | 99.5 |
| Midpoint diameter (mm): | 36.6 | 43.0 |
| No. Of kernel per rows: | 12.56 | 15.74 |
| Row alignment, (1. Straight, 2. Slightly surved, 3. Spiral): | 1.5 | 1.4 |
| Position of the ear 65 days after 50% silk: | Horizontal | Upright |
| Silk color (3 days after emergence): | Red (5R 5/6) | Green-Yellow (2.5GY 8/8) |
| Husk extension, (1. Short, ear exposed) 2. Medium 8 cm, 3. Long 8–10 cm 4. Very long 10 cm) : | 1.8 | 2.3 |
| Taper of ear: | Average | Average |
| Husk color (fresh) 25 days after 50% silking: | Medium-green (5GY 6/8) | Medium-green (5 GY 5/8) |
| Husk color (dry) 65 days after 50% silking: | Green-yellow, Buff | Buff |
| Shank length(cm): | 8.65 | 10.9 |
| Husk tightness (65 days after 50% silk, scale 1–9 1 = loose): | 2.5 | 5.5 |
| F. Kernel (Dried): Size (from ear mid-point): | | |
| Length (mm): | 10.3 | 11.1 |
| Width (mm): | 8.1 | 8.9 |
| Thickness (mm): | 4.4 | 6.4 |
| Shape grade (% rounds): | 44.5 | 48.9 |
| Aleurone color: | Buff, Homozygous (2.5Y 8/4) | Buff, Homozygous (2.5Y, 8/4) |
| Endosperm color: | Yellow-orange (7.5YR 7/10) | Yellow-orange (7.5YR 7/10) |
| Endosperm type: | Normal starch | Normal starch |
| Gm weight/100 seeds (unsized): | 25.5 | 24.6 |
| G. Cob: | | |
| Diameter at mid-point (mm): | 21.3 | 27.9 |
| Color: | Red (10R 6/6) | White (10/) |
| H. Agronomic Traits: | | |
| Stay Green, 65 days after anthesis Scale 1 = worst to 9 = excellent): | 2.5 | 4.0 |
| Root lodging, 65 days after anthesis (%): | 0 | 1.7 |
| Dropped ears, 65 days after anthesis (%): | 0 | 0 |
| I. Disease Resistance: | | |
| Northern leaf blight: *Exserohilum turcicum* | 5 | 7 |
| Grey leaf spot: *Cercospora zea-maydis* | 8 | 5 |

TABLE 1-continued

VARIETY DESCRIPTION INFORMATION FOR INBRED LINE NP 2013 and A 619

|  | NP 2013 | A 619 |
|---|---|---|
| Eye Spot: | 5 | 6 |
| *Kubatiella zeae* | | |
| J. Insect Resistance: | | |
| European Corn Borer | | |
| (*Ostrinia nubilialis*) | | |
| 1st generation: | 3 | 4 |
| 2nd generation: | 4 | 6 |

The above disease and insect resistance description is based on a scale of 1–9; wherein 1–3 is considered susceptible, 4–5 intermediate, 6–7 resistant and 8–9 highly resistant.

With respect to publicly available inbred lines, NP 2013 most closely resembles A619. However, these lines differ in a number of characteristics. The lines differ in flowering maturity, plant height and cob color. While NP 2013 is earlier than A619 and is shorter than A619, it has a red cob compared to A619 which has a white cob. Other characteristics between NP 2013 and A619 are summarized in Table 1.

With respect to proprietary Northrup King inbred lines, NP 2013 most closely resembles NP H8540 and may be distinguished from NP H8540 by numerous characteristics including some of the characteristics listed in Table 2 below. NP 2013 may also be distinguished from NP 911 and NP 912, other closely related proprietary inbred lines having PVP Certificate Nos 9200 12 and 9200013 respectively.

TABLE 2

1994 Variety Comparison Data

| Line | Plt ht (cm) | Ear Ht. (cm) | Silk (HU) | Pollen (HU) | INTL | STGR | GRQU |
|---|---|---|---|---|---|---|---|
| NP 2013 | 178 | 70 | 1297 | 1303 | 2.0 | 6.0 | 2.0 |
| NP 911 | 205 | 70 | 1328 | 1318 | 4.0 | 5.0 | 2.0 |
| NP 912 | 173 | 58 | 1342 | 1335 | 5.0 | 7.0 | 4.0 |
| NP H8540 | 200 | 78 | 1388 | 1398 | 6.0 | 7.0 | 5.0 |
| # reps | 2 | 2 | 3 | 3 | 1 | 2 | 1 |
| LSD (0.5) | 22 | 21 | 56 | 49 | — | 2 | — |

In addition to phenotypic observations, the genotype of a plant can also be examined. There are many techniques available for the analysis, comparison and characterization of plant genotype and these include isozyme electrophoresis, restriction fragment length polymorphism (RFLPs), randomly amplified polymorphic DNAs (RAPDs) sequence characterized amplified regions (SCARs) and amplified fragment length polymorphisms (AFLPs). While many of the techniques are used RFLPs have the advantage of revealing an exceptionally high degree of allelic variation in corn. Moreover there are a tremendous number of markers available to use. Reference is made to Mumm and Dudley, A Classification of 148 U.S. Maize Inbreds: I Cluster Analysis based on RFLP's, Crop Sci., 34:842–851 (1994) and Lee, M "Inbred Lines of Maize and Their Molecular Markers" The Maize Handbook (Springer-Verlag, New York, Inc. 1994 which is hereby incorporated by reference.

Both inbred lines NP 2013 and A619 were subject to a various RFLP probes and the results indicate that the two inbreds have 15 out of 16 loci with different alleles. Additionally, RFLP relationship data indicate that NP 2013 is distinguished from other closely related inbred lines.

This invention is also directed to methods for producing a corn plant by crossing a first parent corn plant with a second parent corn plant, wherein the first or second corn plant is a corn plant of the inbred line NP 2013. However, both first and second parent corn plant can come from the inbred corn line NP 2013. Therefore any methods using NP 2013 are part of this invention including self-pollination, backcross-pollination, hybrid breeding and crosses to populations. It may be desirable to use a male-sterile (either cytoplasmic or nuclear) female parent to prevent self-pollination. If the female is not male-sterile, then either physical or chemical steps may be taken to ensure that self-pollination does not occur. Any plants produced using inbred corn line NP 2013 as a parent are within the scope of this invention including any plant produced by the use of cells, protoplasts or tissue from NP 2013.

Specifically NP 2013 produces hybrids that are competitive yielding. In general, hybrids have good early season vigor, high test weight grain and good stalk quality.

The techniques used to obtain the corn hybrid seeds and plants of this invention are conventional in the seed industry and are well known to those skilled in the art. The two parent lines are planted in pollinating proximity to each other in alternating sets of rows; however, any convenient planting pattern that allows for the free transfer of pollen is acceptable. The plants of both inbred lines are allowed to grow until the time of flowering. At flowering, tassels are removed from all plants of the female parent by hand, machine or other means. Natural cross-pollination is allowed to occur. Ears from the female plants are harvested to obtain novel $F_1$ hybrid corn seeds of the present invention. $F_1$ hybrid corn plants of the invention are obtained by planting seeds harvested from the female plant.

A competitive yielding hybrid of this invention is N1718 wherein NP 2013 is the female parent. The hybrid produced is a 80 Minnesota Relative Maturity single cross hybrid. This hybrid most closely resembles the commercially available Northrup King Co. hybrid PX9060. The hybrid N1718 has significantly yielded more than PX9060 and is significantly better for stalk quality. Another hybrid produced from the cross of NP 2013 wherein the claimed inbred is the female parent N2522. Table 3 below illustrates some characteristics of N1718 and N2522 compared to other similar hybrids.

TABLE 3

Combined Location and Year Performance Data
(1994, 1995; 42 environments; 75–95 RM Markets)

|  | YLD | MST | STK (BR) | RT | DE | SILK | Plt Ht | Ear Ht. | STGR |
|---|---|---|---|---|---|---|---|---|---|
| N1718 | 134 | 20.4 | 8 | 1 | 18 | 1145 | 233 | 95 | 5.0 |
| N2522 | 149 | 22.1 | 9 | 2 | 8 | 1173 | 248 | 90 | 4.3 |
| PX9060 | 122 | 19.3 | 12 | 2 | 5 | 1107 | 228 | 88 | 6.9 |

TABLE 3-continued

Combined Location and Year Performance Data
(1994, 1995; 42 environments; 75–95 RM Markets)

|  | YLD | MST | STK (BR) | RT | DE | SILK | Plt Ht | Ear Ht. | STGR |
|---|---|---|---|---|---|---|---|---|---|
| N1404 | 133 | 21.1 | 8 | 4 | 4 | 1112 | 252 | 96 | 5.2 |
| Pioneer 3962 | 123 | 20.7 | 14 | 4 | 10 | 1088 | 224 | 91 | 7.0 |
| K 127 | 126 | 20.0 | 7 | 3 | 3 | 1101 | 223 | 75 | 6.9 |
| Trials with data: | 42 | 42 | 40 | 36 | 39 | 6 | 6 | 6 | 7 |
| LSD (0.5) | 5 | 0.4 | 2 | 3 | 0 | 32 | 10 | 8 | 0.9 |

STGR = Stay green, a measure of plant health based on a scale of 1–9 wherein 1 is excellent and 9 is poor.

As used herein the term plant includes plant cells, plant protoplasts, plant cell tissue cultures including that from which corn plants fertile or otherwise can be regenerated, plant calli and plant cell clumps, and differentiated forms of plants such as, but not limited to embryos, pollen, stamen, anthers, flowers, kernels, ears, cobs, leaves, stalks, roots, shoots, plantlets, silks and kernels. In this context, the invention also includes a corn plant regenerated from any NP 2013 corn cell, protoplast and tissue mentioned above and having the same genotype as NP 2013.

Methods of cell and tissue culture and regeneration are well known in the art and described for example in "Plant Tissue Culture Manual: Fundamentals and Application", Ed. K. Lindsey, Kluwer (1991) and in Green and Rhodes, "Plant Regeneration in Tissue Culture of Maize", Maize for Biological Research (Plant Molecular Biology Association, Charlottesville, Va., 1982, pp. 367–372), which are hereby incorporated by reference.

As is well known corn can be put to a wide variety of uses not only as livestock feed but also for human consumption of corn kernels and as a raw material in industry. Both grain and non-grain portions of the plant are used as a livestock feed for swine, cattle and poultry. In the food industry corn is used in wet and dry milling. In wet milling there is the separation of the germ, hull gluten and starch. Germ is used to produce corn oil and germ cake for feed. Corn starch may be packaged for human consumption or used in food products such as sauces, gravies, puddings, sweeteners, syrups, and baking powder. Other nonedible uses include textiles, paper, adhesives, cosmetics, explosives, corn binders, laundry purposes and agricultural formulations. Dry milling is used to produce breakfast foods, grits, cornmeal and corn flour. Other uses of corn include fuel, in the form of fuel alcohol or ethanol; seed; alcoholic beverages and construction.

DEPOSIT INFORMATION

Deposits of at least 2500 seeds of inbred NP 2013, has been made unrestrictedly available to the public via the American Type Culture Collection (ATCC), Rockville, Md. 20852 U.S.A. The deposit corresponds to ATCC Deposit No. 209541, and was made on 209541. The seeds are from stock maintained by Northrup King, Golden Valley, Minn., since prior to filing this application or any parents thereof. The deposit of inbred corn line NP 2013 will be maintained in the ATCC depository, which is a public depositary, for a period of 30 years, or 5 years after the most recent request, or for the effective life of the patent, whichever, is longer, and will be replaced if it ever becomes nonviable during that period. Additionally, Applicant does not waive any infringement of its rights granted under this patent or under the Plant Variety Protection Act (7 U.S.C. 2312 et seq.) for any PVP certificate received and applied for.

It is claimed:

1. An inbred corn line designated NP2013, the seeds of which have been deposited as ATCC Accession No. 209541.

2. A corn plant or plant parts of inbred corn line designated NP2013 of claim 1.

3. A corn plant having all physiological and morphological characteristics of the plant of claim 2.

4. Seeds of the inbred corn line NP 2013 of claim 1.

5. An ovule of the plant of claim 2.

6. Pollen of the plant of claim 2.

7. A tissue culture comprising regenerable cells of the plant according to claim 2.

8. A corn plant regenerated from the cells or protoplasts of a culture of corn tissue capable of expressing all the physiological and morphological characteristics of the corn plant of claim 2, the seed of which has been deposited and having ATCC Accession No. 209541.

9. Hybrid seed produced by crossing plants of inbred corn line designated NP2013, the seed having ATCC Accession No. 209541. and plants of another inbred corn line having a genotype different from corn line NP2013.

10. Hybrid seed of claim 9 wherein the corn line NP 2013 is the female parent.

11. Hybrid corn plants grown from the seed of claim 9.

12. A tissue culture of regenerable cells of the corn plant of claim 11.

13. A first generation hybrid corn plant produced by growing hybrid corn seed, wherein said seed is produced by crossing a first inbred parent corn plant with a second inbred parent corn plant wherein said first or second inbred corn plant is the corn plant of claim 2 and harvesting the resultant hybrid seed.

14. The first generation hybrid corn plant of claim 13 wherein the corn plant of inbred corn line NP 2013 is the female parent corn plant.

15. Hybrid corn seeds produced by the process of:
  A. planting in pollinating proximity seeds of inbred corn line NP2013 having ATCC Accession No. 209541 and a second inbred line having a genotype different from NP2013;
  B. cultivating corn plants resulting from said planting until time of flowering;
  C. emasculating said flowers of plants of one of the corn inbred lines;
  D. allowing cross pollination to occur between said inbreds, and
  E. harvesting the seeds produced on said plants.

16. Hybrid corn plants produced by growing the seeds of claim 15.

17. A first generation (F1) hybrid corn plant produced by the process of:

A. planting in pollinating proximity seeds of inbred corn line NP2013 having ATCC Accession No. 209541 and a second inbred line having a genotype different from NP2013;

B. cultivating corn plants resulting from said planting until time of flowering;

C. emasculating said flowers of plants of one of the corn inbred lines;

D. allowing cross pollination to occur between said inbreds, and

E. harvesting the seeds produced on said plants of inbred corn line NP 2013 and

F. growing a harvested seed of step e.

18. A corn plant regenerate from the cells or protoplasts of a culture of corn tissue capable of expressing all the physiological and morphological characteristics of the hybrid corn plant of claim 17.

* * * * *